(12) United States Patent
Lee et al.

(10) Patent No.: US 12,586,479 B2
(45) Date of Patent: Mar. 24, 2026

(54) APPARATUS AND METHOD FOR ENHANCING MEMORY BASED ON ELECTROENCEPHALOGRAM

(71) Applicant: Korea University Research and Business Foundation, Seoul (KR)

(72) Inventors: Seong Whan Lee, Seoul (KR); Gi Hwan Shin, Daegu (KR); Young Seok Kweon, Incheon (KR); Heon Gyu Kwak, Namyangju-si (KR); Ha Na Jo, Seoul (KR)

(73) Assignee: KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 13 days.

(21) Appl. No.: 18/515,941

(22) Filed: Nov. 21, 2023

(65) Prior Publication Data

US 2024/0169851 A1 May 23, 2024

(30) Foreign Application Priority Data

| | | |
|---|---|---|
| Nov. 21, 2022 | (KR) | ........................ 10-2022-0156743 |
| Aug. 18, 2023 | (KR) | ........................ 10-2023-0108140 |

(51) Int. Cl.
| | |
|---|---|
| *G09B 5/02* | (2006.01) |
| *A61B 5/00* | (2006.01) |
| *A61B 5/374* | (2021.01) |

(52) U.S. Cl.
CPC ................ *G09B 5/02* (2013.01); *A61B 5/374* (2021.01); *A61B 5/6803* (2013.01)

(58) Field of Classification Search
CPC .......... G09B 5/02; A61B 5/374; A61B 5/6803
See application file for complete search history.

(56) References Cited

U.S. PATENT DOCUMENTS

| | | | |
|---|---|---|---|
| 11,344,696 B2 * | 5/2022 | Choi | .................... A61N 5/0618 |
| 2021/0166577 A1 * | 6/2021 | Hong | .................. A61B 5/6803 |
| 2022/0312406 A1 * | 9/2022 | Kim | ...................... H04W 76/20 |

FOREIGN PATENT DOCUMENTS

| | | |
|---|---|---|
| KR | 10-2021-0103371 A | 8/2021 |
| KR | 10-2022-0089037 A | 6/2022 |
| KR | 10-2023-0034098 A | 3/2023 |

OTHER PUBLICATIONS

Office Action dated Mar. 20, 2025 for corresponding Korean Patent Application No. 10-2023-0108140, along with an English translation (12 pages).

* cited by examiner

*Primary Examiner* — Xuan M Thai
*Assistant Examiner* — Sadaruz Zaman
(74) *Attorney, Agent, or Firm* — HAUPTMAN HAM, LLP

(57) ABSTRACT

Disclosed is an apparatus for memory enhancement based on electroencephalogram according to one embodiment of the present invention. According to the present invention, it is possible to identify forgotten items during retrieval in a re-learning process based on a user's brain signals measured in an initial learning process by means of a brain signal measurement unit capable of measuring brain signals, and provide the user with repetitive learning depending on the user's electrophysiological characteristics, resulting in a more effective enhancement of memory.

9 Claims, 8 Drawing Sheets

FIG. 4

| Layer | Operation | Size of feature map | Kernel size |
|---|---|---|---|
| 0 | Input | 6 x 10 x 9 | — |
| 1 | Convolution<br>Batch normalization | 8 x 8 x 7 | 3 x 3 |
| 2 | Convolution<br>Batch normalization | 64 x 6 x 5 | 3 x 3 |
| 3 | Max-pooling<br>Dropout (0.3) | 64 x 3 x 2 | 1 x 2 |
| 4 | Flatten | 384 | — |
| 5 | Fully-connected | 2 | — |

APPARATUS AND METHOD FOR ENHANCING MEMORY BASED ON ELECTROENCEPHALOGRAM

CROSS-REFERENCE TO RELATED APPLICATION

The present application claims the benefit of priority to Korean Patent Application No. 10-2022-0156743, filed on Nov. 21, 2022 and Korean Patent Application No. 10-2023-0108140, filed on Aug. 18, 2023 in the Korean Intellectual Property Office. All of the aforementioned applications are hereby incorporated by reference in their entireties.

BACKGROUND OF THE INVENTION

1. Field of the Invention

The present invention relates to an apparatus and method that can help enhance a user's memory during re-retrieval in a memory task using electroencephalogram (EEG) that is an electrophysiological signal. More specifically, the present invention relates to an apparatus and method for memory enhancement based on electroencephalogram, involving performing encoding during initial learning through a mobile phone application and then performing retrieval and re-encoding while wearing a headband capable of measuring brain signals. Furthermore, the present invention relates to an apparatus and method that maximizes the user's learning efficiency by classifying the presence or absence of memory during re-retrieval from a classification model that has learned the characteristics of the measured brain signals and presenting repetitive learning to the user.

2. Description of the Related Art

In general, vocabulary learning is considered the most fundamental aspect of language learning. Learners engage in simple studies using dictionaries and textbooks or perform vocabulary learning through mobile phone applications. However, the majority of learning is uniform and does not take into account the neurophysiological characteristics and individual traits of the learners.

Memory is a crucial component in learning and decision-making, and is a comprehensive cognitive process of encoding and retrieving new information in the brain. Specifically, encoding refers to the initial experience of recognizing and learning information, while retrieval refers to the mental process of retrieving previously learned information. Furthermore, memory is classified into short-term and long-term memory over time, each having different neurophysiological activity patterns. Memory impairment is associated with many diseases such as dementia and Parkinson's disease, and ultimately, it is a significant issue that can reduce the quality of our lives. To address these issues, there is a need for devices and technologies that can enhance the memory to alleviate memory impairments and increase the efficiency of learning.

Traditionally, functional magnetic resonance imaging (fMRI) has been predominantly used to understand the memory process. While fMRI is efficient in observing changes in brain activation areas over space, its low temporal resolution makes it difficult to identify rapidly changing brain features. Moreover, the need for specialized laboratories due to the size of the equipment imposes limitations, making it inefficient.

Therefore, electroencephalography has recently been used, which is cost-effective and features high temporal resolution. Electroencephalography is a non-invasive method that involves measuring the electrical activity of the brain from electrodes attached to the surface of the head, and research investigating the brain activity mechanism of human memory processes in the fields of cognitive and neuroscience, utilizing the measured bioelectrical signals, is gaining attention.

Electroencephalogram appears in the form of highly complex oscillatory waveforms, which are difficult to interpret intuitively. Power spectral density (PSD) is commonly used to interpret electroencephalograms based on their frequencies. PSD assumes that the electroencephalogram is a combination of simple linear oscillations and decomposes the signal into its frequency components, representing the magnitude or power of each frequency. This allows the classification and understanding of electroencephalogram based on the frequency and amplitude.

Frequencies related to memory include theta waves in the range of 4 to 8 Hz. Theta waves play a role in regulating the flow of information and assisting in information processing between brain regions. Moreover, it may be related to acetylcholine, a neurotransmitter necessary for memory formation, and acetylcholine is a neurotransmitter that plays a critical role in learning and memory. The association between theta waves and memory has a significant impact on brain wave analysis and memory research and is utilized for purposes such as improving memory function and advancing neuroscience studies.

For example, many studies have found statistical differences in the electroencephalogram between remembered items and forgotten items. This demonstrates that brain signals measured during a memory task can determine the characteristics related to memory recognition processes.

The existing standardized educational approaches have limitations as they do not take into account the individual characteristics of each learner, making it difficult to clearly understand the causes of performance changes. Moreover, in the case of technologies that involve delivering subtle electrical signals, there may be side effects, leading to potential discomfort or resistance from the user's perspective.

Therefore, there is a demand for a technology that improves existing standardized educational approaches by using brain signals related to memory cognition and at the same time ensures that users do not experience discomfort or resistance.

SUMMARY OF THE INVENTION

The present invention has been made in an effort to solve the above-described problems and to meet the demand for technology that improves existing standardized educational approaches by using brain signals related to memory cognition and at the same time ensures that users do not experience discomfort or resistance, and an object of the present invention is to provide an apparatus and method for memory enhancement based on electroencephalogram, which identifies forgotten items during retrieval in a re-learning process based on a user's brain signals measured in an initial learning process by means of a brain signal measurement unit capable of measuring brain signals, and provides the user with repetitive learning depending on the user's electrophysiological characteristics, resulting in a more effective enhancement of memory.

The above-mentioned objects of the present invention are not limited to those mentioned above, and other objects not mentioned will be clearly understood by those skilled in the art from the following description.

To achieve the above-mentioned objects, one embodiment of the present invention provides an apparatus for memory enhancement based on electroencephalogram, the apparatus comprising: a brain signal measurement unit that measures a user's brain signal; a preprocessing unit that extracts theta waves from the brain signal through power spectrum analysis (PSD); a memory ability determination unit that determines the user's memory ability based on the theta waves extracted by the preprocessing unit; a communication unit that transmits first encoding information to a user terminal and receives first retrieval information corresponding to the first encoding information from the user terminal; and a learning method providing unit that provides a learning method tailored to the user's memory ability based on the determination result of the memory ability determination unit, wherein the brain signal measurement unit measures the user's brain signal (hereinafter referred to as a first brain signal) if the communication unit receives the first retrieval information corresponding to the first encoding information from the user terminal, and the memory ability determination unit determines the user's memory ability based on the extraction result of theta waves (hereinafter referred to as a first theta wave extraction result) extracted by the preprocessing unit from the measurement result of the first brain signal.

According to one embodiment, the memory ability determination unit may determine the user's memory ability based on at least one of the user's brain activation result measured by the brain signal measurement unit, the performance according to the brain activation, and the response time according to the brain activation.

According to one embodiment, the communication unit may transmit second encoding information to the user terminal and receive second retrieval information corresponding to the second encoding information from the user terminal, the brain signal measurement unit may measure the user's brain signal (hereinafter referred to as a second brain signal) if the communication unit transmits the second encoding information to the user terminal and measure the user's brain signal (hereinafter referred to as a third brain signal) if the communication unit receives the second retrieval information corresponding to the second encoding information from the user terminal, and the memory ability determination unit may determine the user's memory ability based on the extraction result of theta waves (hereinafter referred to as a second theta wave extraction result) extracted by the preprocessing unit from the measurement result of the second brain signal and determine the user's memory ability based on the extraction result of theta waves (hereinafter referred to as a third theta wave extraction result) extracted by the preprocessing unit from the measurement result of the third brain signal.

According to one embodiment, the brain signal measurement unit may be configured in the form of a headband that the user can wear, wherein an electroencephalogram sensor may be attached to the inner side of the headband to measure the user's brain signal, and Velcro may be attached to the outer side of the headband.

According to one embodiment, the communication unit may receive third retrieval information corresponding to the first encoding information from the user terminal within a predetermined reference time if the user's memory ability determined by the memory ability determination unit is short-term memory ability, the brain signal measurement unit may measure the user's brain signal (hereinafter referred to as a fourth brain signal) if the communication unit receives the third retrieval information corresponding to the first encoding information from the user terminal within a predetermined reference time, the memory ability determination unit may determine the user's long-term memory ability based on the extraction result of theta waves (hereinafter referred to as a fourth theta wave extraction result) extracted by the preprocessing unit from the measurement result of the fourth brain signal, and the learning method providing unit may provide a learning method tailored to the user's long-term memory ability.

According to one embodiment, the apparatus may comprise a storage unit that stores information about the user's memory ability determined by the memory ability determination unit, wherein the memory ability determination unit may classify the determination results of the user's memory ability based on a predetermined classification criterion, and the storage unit may store the classification result of the memory ability determination unit.

According to one embodiment, the memory ability determination unit may compare the first theta wave extraction result and the second theta wave extraction result and determine the user's memory ability based on the comparison result.

According to one embodiment, the communication unit may receive fourth retrieval information corresponding to the second encoding information from the user terminal if the memory ability determination unit determines that the second retrieval information corresponding to the second encoding information received from the user terminal is not a correct answer, the brain signal measurement unit may measure the user's brain signal (hereinafter referred to as a fifth brain signal) if the communication unit receives the fourth retrieval information corresponding to the second encoding information from the user terminal, and the memory ability determination unit may determine the user's memory ability based on the extraction result of theta waves (hereinafter referred to as a fifth theta wave extraction result) extracted by the preprocessing unit from the measurement result of the fifth brain signal.

According to one embodiment, the learning method providing unit may provide a learning method tailored to the user based on the comparison result of the memory ability determination unit.

To achieve the above-mentioned objects, another embodiment of the present invention provides a method for memory enhancement based on electroencephalogram, the method comprising the steps of: transmitting, by a communication unit, first encoding information to a user terminal; receiving, by the communication unit, first retrieval information corresponding to the first encoding information from the user terminal; measuring, by a brain signal measurement unit, a user's brain signal (hereinafter referred to as a first brain signal) if the communication unit receives the first retrieval information corresponding to the first encoding information from the user terminal; extracting, by a preprocessing unit, theta waves from the first brain signal; and determining, by a memory ability determination unit, the user's memory ability based on the extraction result of theta waves (hereinafter referred to as a first theta wave extraction result) extracted by the preprocessing unit from the measurement result of the first brain signal.

According to the present invention as described above, it is possible to identify forgotten items during retrieval in a re-learning process based on a user's brain signals measured in an initial learning process by means of a brain signal measurement unit capable of measuring brain signals, and provide the user with repetitive learning depending on the user's electrophysiological characteristics, resulting in a more effective enhancement of memory.

The effects of the present invention are not limited to the effects mentioned above, and other effects not mentioned will be clearly understood by those skilled in the art from the description below.

BRIEF DESCRIPTION OF THE DRAWINGS

The above and other features and advantages of the present invention will become more apparent by describing in detail exemplary embodiments thereof with reference to the attached drawings in which:

FIG. 4 is a diagram illustrating a convolutional neural network structure;

DETAILED DESCRIPTION OF THE INVENTION

Figure 1:
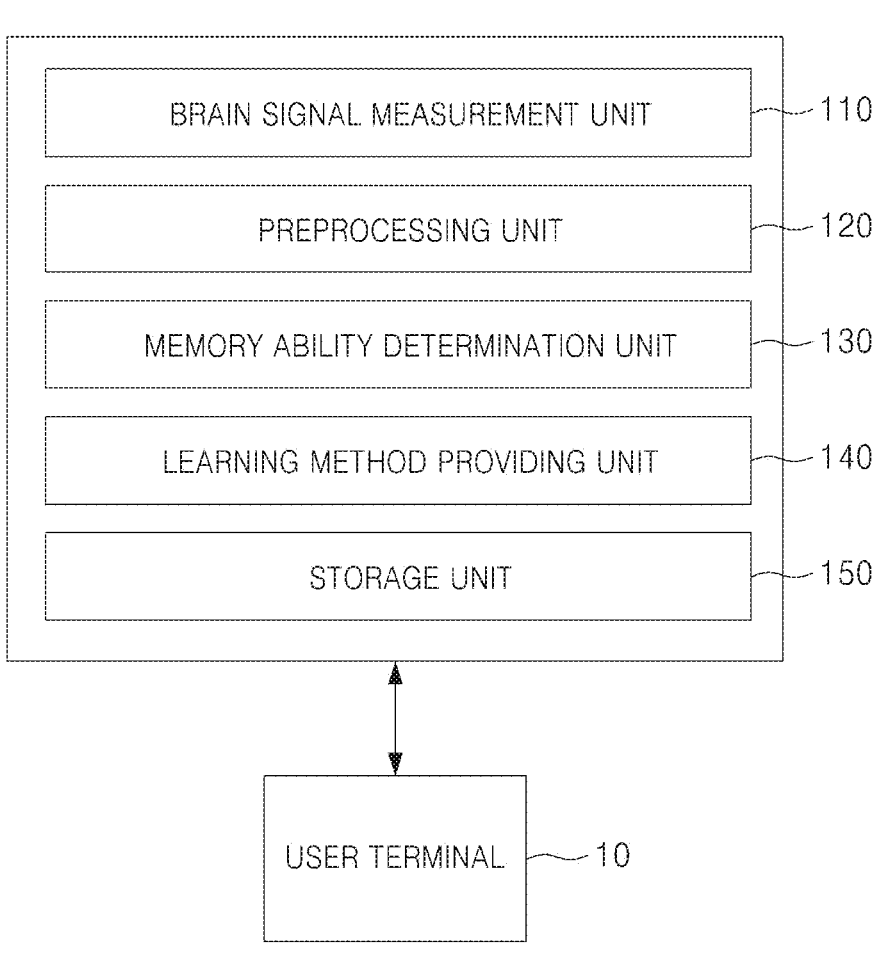
FIG. 1 is a diagram illustrating the overall configuration of an apparatus for memory enhancement based on electroencephalogram according to a first embodiment of the present invention.

Details regarding the objects and technical features of the present invention and the resulting effects will be more clearly understood from the following detailed description based on the drawings attached to the specification of the present invention. Preferred embodiments according to the present invention will be described in detail with reference to the attached drawings.

The embodiments disclosed in this specification should not be construed or used as limiting the scope of the present invention. It is obvious to those skilled in the art that the description, including the embodiments, of this specification has various applications. Therefore, any embodiments described in the detailed description of the present invention are illustrative to better illustrate the present invention and are not intended to limit the scope of the present invention to the embodiments.

The functional blocks shown in the drawings and described below are only examples of possible implementations. In other implementations, different functional blocks may be used without departing from the spirit and scope of the detailed description. Moreover, although one or more functional blocks of the present invention are shown as individual blocks, one or more of the functional blocks of the present invention may be a combination of various hardware and software components that perform the same function.

Furthermore, the term "comprising" certain components, which is an "open-ended" term, simply refers to the presence of the corresponding components, and should not be understood as excluding the presence of additional components.

In addition, if a specific component is referred to as being "connected" or "coupled" to another component, it should be understood that it may be directly connected or coupled to another other component, but there may be other components therebetween.

Hereinafter, preferred embodiments of the present invention will be described in detail with reference to the accompanying drawings.

Figure 2:
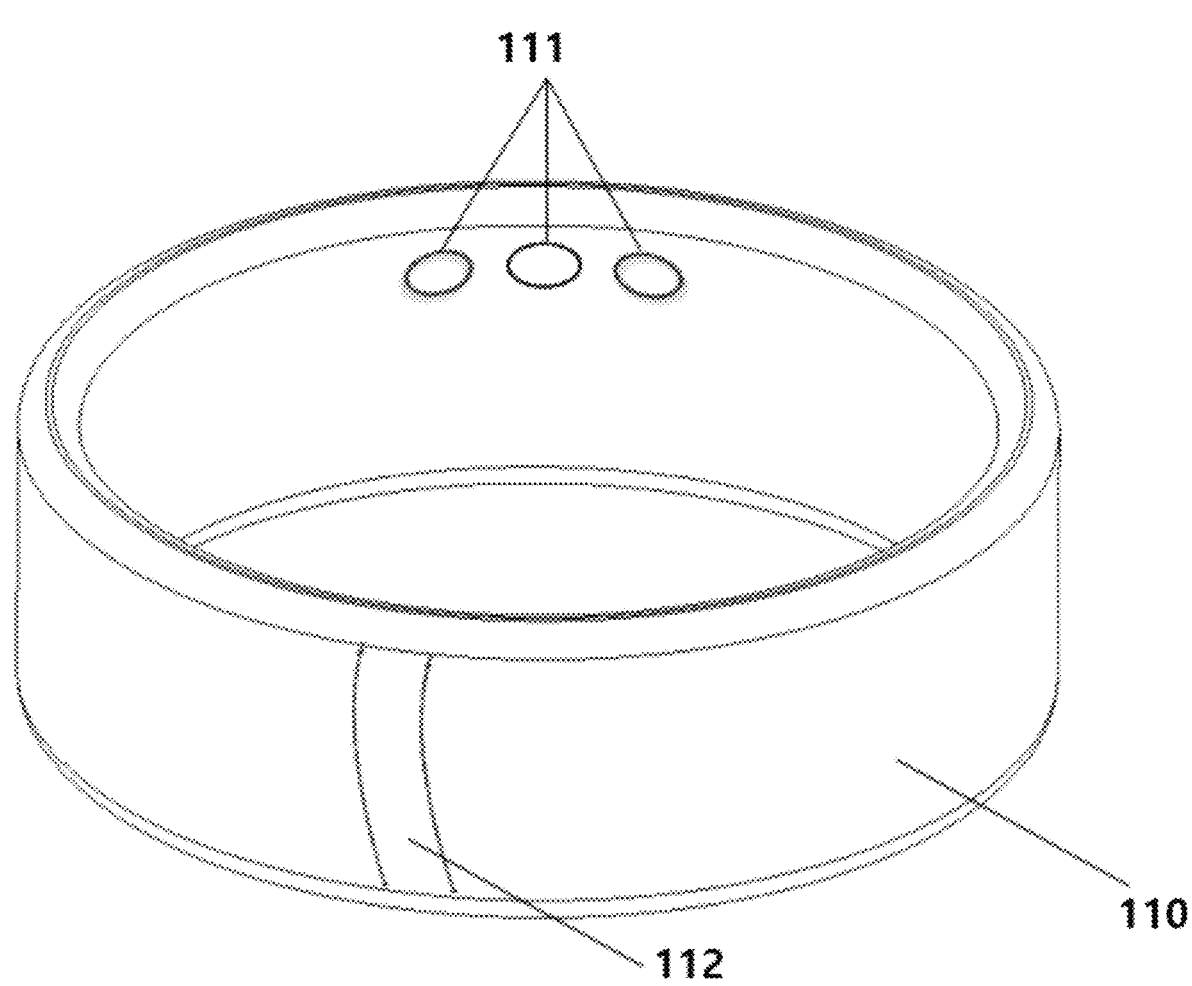
FIG. 2 is a diagram illustrating the configuration of a brain signal measurement unit of the apparatus for memory enhancement based on electroencephalogram according to the first embodiment of the present invention.
Figure 3:
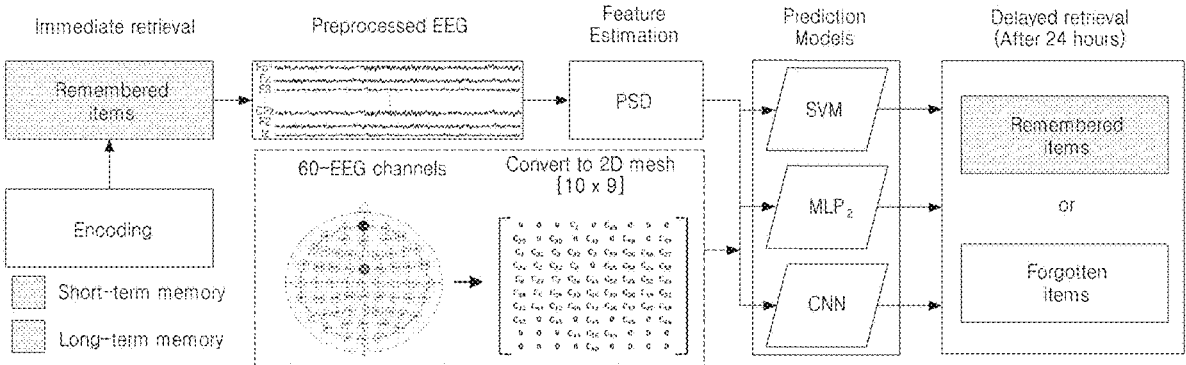
FIG. 3 is a diagram illustrating how a memory ability determination unit, which is a component of the apparatus for memory enhancement based on electroencephalogram according to the first embodiment of the present invention, predicts long-term memory from short-term memory.
Figure 5A:
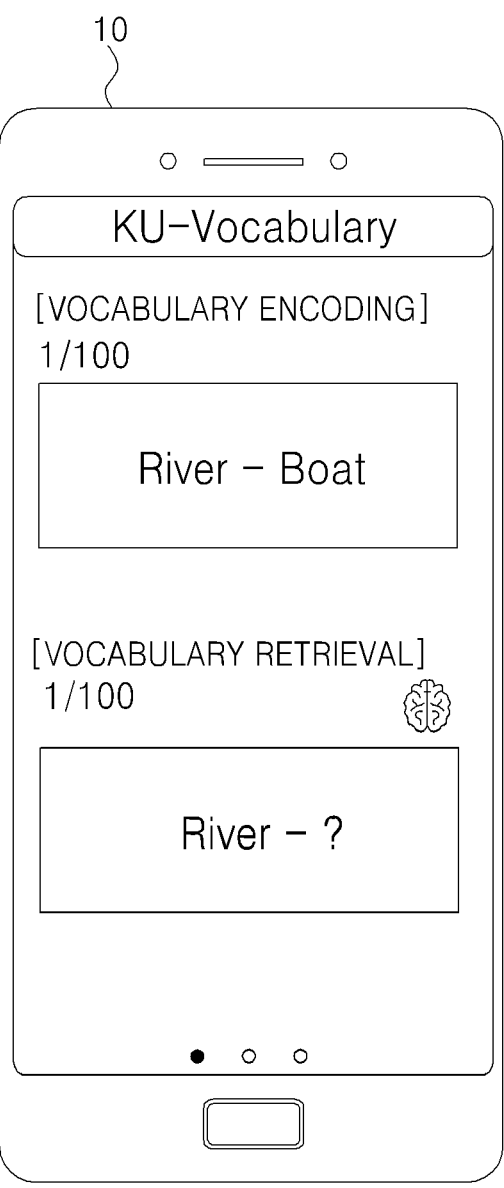
FIGS. 5A, 5B and 5C are diagrams illustrating the encoding, retrieval, and re-retrieval processes for the user and the brain activation result performed by the apparatus for memory enhancement based on electroencephalogram according to the first embodiment of the present invention.
Figure 5B:
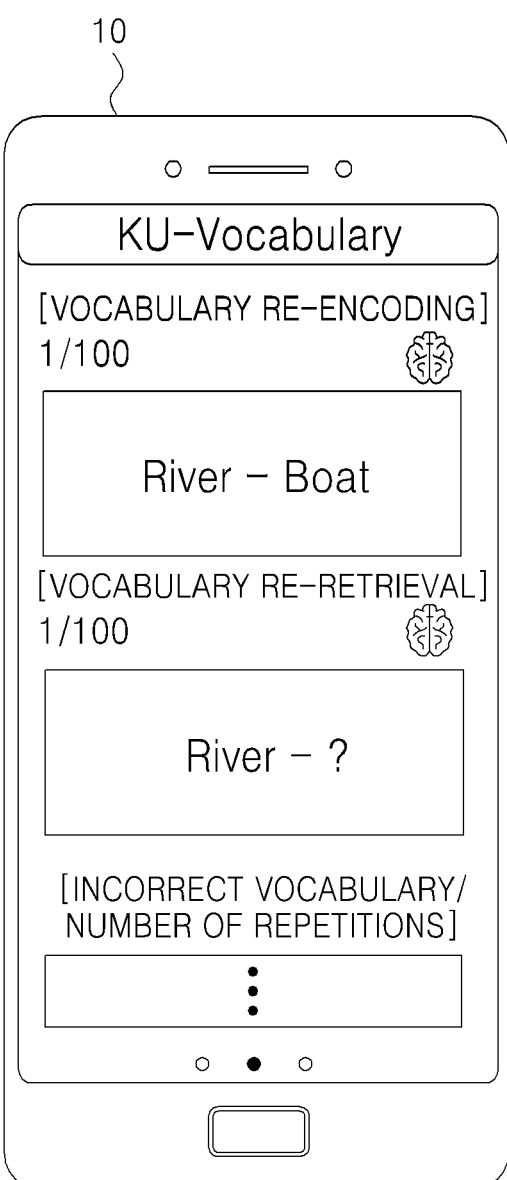
Figure 5C:
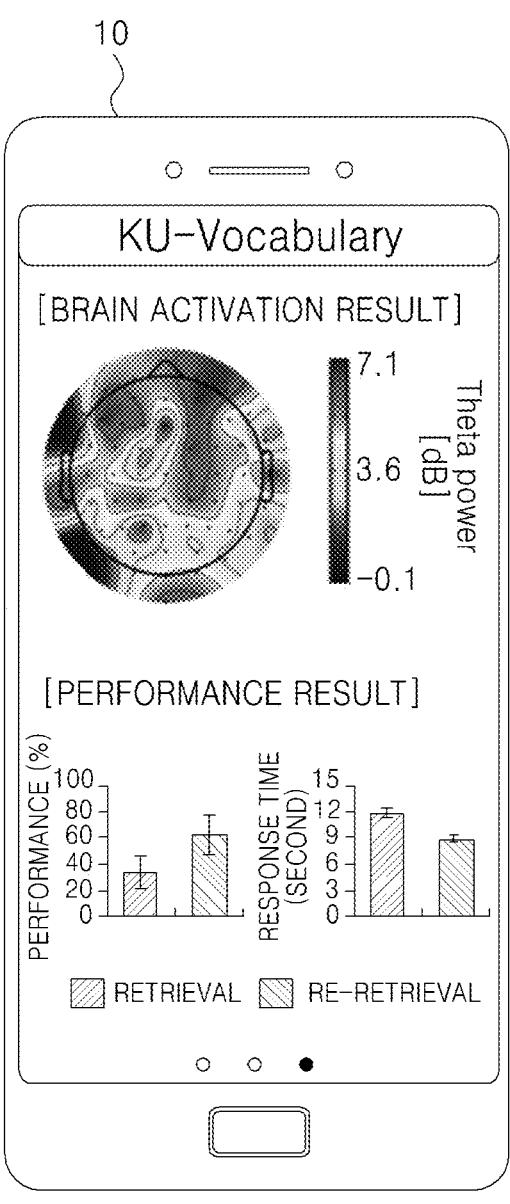

FIG. 1 is a diagram illustrating the overall configuration of an apparatus for memory enhancement based on electroencephalogram according to a first embodiment of the present invention; FIG. 2 is a diagram illustrating the configuration of a brain signal measurement unit of the apparatus for memory enhancement based on electroencephalogram according to the first embodiment of the present invention; FIG. 3 is a diagram illustrating how a memory ability determination unit, which is a component of the apparatus for memory enhancement based on electroencephalogram according to the first embodiment of the present invention, predicts long-term memory from short-term memory; FIG. 4 is a diagram illustrating a convolutional neural network structure; and FIGS. 5A, 5B and 5C are diagrams illustrating the encoding, retrieval, and re-retrieval processes for the user and the brain activation result performed by the apparatus for memory enhancement based on electroencephalogram according to the first embodiment of the present invention.

However, this is merely a preferred embodiment to achieve the object of the present invention, and it is understood that some components may be added or deleted as needed and one component's role may be performed in conjunction with another component.

The apparatus 100 for memory enhancement based on electroencephalogram according to the first embodiment of the present invention may comprise a processor (not shown), a network interface (not shown), a memory (not shown), a storage (not shown), and a data bus (not shown) connecting these components. Moreover, it may also include other additional components required to achieve the objects of the present invention.

The processor (not shown) may control the overall operation of each component. The processor (not shown) may be any one of a central processing unit (CPU), a microprocessor unit (MPU), a microcontroller unit (MCU), or an artificial intelligence processor commonly known in the art to which the present invention pertains. Furthermore, the processor (not shown) may perform operations for at least one application or program to perform the various functions which will be described with respect to an apparatus 100 for memory enhancement based on electroencephalogram according to the first embodiment of the present invention.

The network interface (not shown) may support wired and wireless Internet communications for the apparatus 100 for memory enhancement based on electroencephalogram according to the first embodiment of the present invention and may also support other known communication methods. Therefore, the network interface (not shown) may be configured to include a corresponding communication module.

The memory (not shown) may store various information, commands and/or information and load one or more computer programs from the storage (not shown) to perform a method for memory enhancement based on electroencephalogram according to a second embodiment of the present invention.

The memory (not shown) may be composed of RAM, but is not limited thereto, and it should be noted that various storage media can also be used as the memory (not shown).

The storage (not shown) may non-temporarily store one or more computer programs and large-capacity network information. This storage may be any one of a nonvolatile memory, such as a read only memory (ROM), an erasable programmable ROM (EPROM), an electrically erasable programmable ROM (EEPROM), and a flash memory, a hard disk drive (HDD), a solid-state drive (SSD), a removable disk, or a computer-readable recording medium commonly known in the art to which the present invention pertains.

Moreover, the storage (not shown) may be implemented as a storage unit 150, which is a component of the apparatus 100 for memory enhancement based on electroencephalogram according to the first embodiment of the present invention, which will be described later.

The data bus (not shown) serves as a pathway for the movement of commands and/or information between the processor (not shown), the network interface (not shown), the memory (not shown), and the storage (not shown) as described above.

The apparatus 100 for memory enhancement based on electroencephalogram according to the first embodiment of the present invention as briefly described above may be in the form of a stand-alone device, for example, an electronic device or a server (including a cloud server). In this context, the electronic devices may include not only devices such as desktop PCs and server devices that are fixedly installed and used in one place, but also portable devices that are easy to carry, such as smartphones, tablet PCs, laptop PCs, PDAs, and PMPs, and it is suitable for any electronic device that includes a CPU corresponding to the processor and has a network function.

Furthermore, the apparatus 100 for memory enhancement based on electroencephalogram according to the first embodiment of the present invention is shown as a single apparatus for the convenience of illustration, but is not limited to a single apparatus, and the respective components of the apparatus 100 for memory enhancement based on electroencephalogram can be distributed over multiple devices.

It should be noted that the apparatus 100 for memory enhancement based on electroencephalogram according to the first embodiment of the present invention is hereinafter referred to as the "apparatus", but the term "apparatus" as used herein may have the same meaning as the processor, and while it is named as an "apparatus", it may be configured as a system implemented by a plurality of apparatuses.

Referring to FIG. 1, the apparatus 100 for memory enhancement based on electroencephalogram according to the first embodiment of the present invention may comprise a brain signal measurement unit 110, a preprocessing unit 120, a memory ability determination unit 130, a learning method providing unit 140, and a storage unit 150, and may further comprise other additional components required to achieve the object of the present invention.

More specifically, the brain signal measurement unit 110 may measure a user's brain signal. In order to measure the user's brain signal, the brain signal measurement unit 110 may be configured in the form of a headband that the user can wear, as can be seen through FIG. 2, and an electroencephalogram sensor 111 may be attached to the inner side of the headband to measure the brain signal of the user wearing the brain signal measurement unit 110.

Here, although there are three electroencephalogram sensors 111, this is for the convenience of illustration, and the number of electroencephalogram sensors 111 will not be limited to three.

Moreover, if the brain signal measurement unit 110 is configured in the form of a headband, Velcro 112 may be attached to the outer surface of the headband for the adjustment of the headband's length.

Furthermore, the brain signal measurement unit 110 may include a communication module (not shown) to transmit and receive data to and from various devices and components.

Here, the communication module (not shown) may be composed of either a wired communication module or a wireless communication module, and it is not limited to the use of a specific communication method.

The preprocessing unit 120 may extract theta waves from the brain signal measured by the brain signal measurement unit 110 through power spectrum analysis.

Here, the preprocessing unit 120 may perform the power spectrum analysis using Equation 1 below, enabling the extraction of theta waves from the brain signal measured by the brain signal measurement unit 110:

$$PSD_{f_1 - f_2} = 10 * \log_{10} 2(\int_{f_1}^{f_2} |\hat{x}(2\pi f)|^2 df) \qquad \text{Equation 1}$$

In Equation 1, $f_1$ may represent a low frequency, $f_2$ may represent a high frequency, and $\hat{x}$ may represent a value obtained by fast Fourier transform.

The memory ability determination unit 130 may determine the user's memory ability based on the theta waves extracted by the preprocessing unit 120.

The communication unit may transmit first encoding information to a user terminal 10.

Here, the communication unit may be composed of either a wired communication module or a wireless communication module, and it is not limited to the use of a specific communication method.

The user terminal 10 may be implemented not only as a device such as a desktop PC, server device, etc., but also as a portable device such as a smartphone, tablet PC, laptop PC, PDA, PMP, etc.

The communication unit may receive first retrieval information corresponding to the first encoding information from the user terminal 10.

Here, the first encoding information may refer to encoding information initially provided to the user, and the first retrieval information may refer to retrieval information corresponding to the encoding information initially provided to the user.

The learning method providing unit 140 may provide a learning method tailored to the user's memory ability based on the determination result of the memory ability determination unit 130.

The brain signal measurement unit 110 may measure the user's brain signal (hereinafter referred to as a first brain signal) if the communication unit receives the first retrieval information corresponding to the first encoding information from the user terminal 10.

The preprocessing unit 120 may extract theta waves from the measurement result of the first brain signal, and the memory ability determination unit 130 may determine the user's memory ability based on the extraction result of theta waves (hereinafter referred to as a first theta wave extraction result) extracted by the preprocessing unit 120 from the measurement result of the first brain signal.

The memory ability determination unit 130 may determine the user's memory ability based on at least one of the user's brain activation result measured by the brain signal measurement unit 110, the performance according to the brain activation, and the response time according to the brain activation.

The communication unit may transmit second encoding information to the user terminal 10, and the communication unit may receive second retrieval information corresponding to the second encoding information from the user terminal 10.

Here, the second encoding information may refer to the encoding information provided to the user for the first time after the first encoding information, and the second retrieval information may refer to retrieval information corresponding to the second encoding information provided to the user for the second time.

The brain signal measurement unit 110 may measure the user's brain signal (hereinafter referred to as a second brain signal) if the communication unit transmits the second encoding information to the user terminal 10 and measure the user's brain signal (hereinafter referred to as a third brain signal) if the communication unit receives the second retrieval information corresponding to the second encoding information from the user terminal 10.

The memory ability determination unit 130 may determine the user's memory ability based on the extraction result of theta waves (hereinafter referred to as a second theta wave extraction result) extracted by the preprocessing unit 120 from the measurement result of the second brain signal.

Moreover, the memory ability determination unit 130 may determine the user's memory ability based on the extraction result of theta waves (hereinafter referred to as a third theta wave extraction result) extracted by the preprocessing unit 120 from the measurement result of the third brain signal.

Through the process of determining the user's memory ability by the memory ability determination unit 130, the present invention can determine the user's memory ability by analyzing the user's brain activity based on the brain signals measured at the point in time when the user terminal 10 transmits the first retrieval information corresponding to the first encoding information, which signifies encoding new information into the brain during the initial learning process, to the communication unit.

Furthermore, similar to the process as described above where the communication unit transmits and receives the second encoding information and the second retrieval information corresponding to the second encoding information, the present invention can determine the user's memory ability by analyzing the user's brain activity based on the brain signals measured, respectively, at the point in time when the user terminal 10 receives the second encoding information from the communication unit and at the point in time when the user terminal 10 transmits the second retrieval information.

In addition, through this process, the present invention can determine the user's brain activation results by analyzing the user's brain activity during the first retrieval process for the user and analyzing the user's brain activity during the second encoding process and the second retrieval process, allowing the memory ability determination unit 130 to effectively determine the user's memory ability at each point in time.

The communication unit may receive third retrieval information corresponding to the first encoding information transmitted to the user terminal 10 if the user's memory ability determined by the memory ability determination unit 130 is short-term memory ability.

In the case of short-term memory, it may mean that the communication unit has received the retrieval information corresponding to the encoding information transmitted to the user terminal 10 within a predetermined time for the determination of short-term memory.

The predetermined time for the determination of short-term memory may be set to 1 hour, for example. However, the mentioned 1 hour is just an example and may not be limited to a specific time.

Moreover, in the case of long-term memory, it may mean that the communication unit has received the retrieval information corresponding to the encoding information transmitted to the user terminal 10 after a predetermined time for the determination of short-term.

The predetermined time for the determination of long-term may be set to 24 hours, for example. However, the mentioned 24 hours is just an example and may not be limited to a specific time.

Moreover, if the user' memory ability determined by the memory ability determination unit 130 is short-term memory ability, the memory ability determination unit 130 may predict the user's long-term memory ability based on the user's short-term memory ability determined by the memory ability determination unit 130.

A more detailed description will now be provided with reference to FIG. 3.

The communication unit may transmit the first encoding information to the user terminal 10 (Encoding), and the communication unit may receive the first retrieval information corresponding to the first encoding information from the user terminal 10 (Remembered items).

Here, as for "Remembered items", it would mean that the first retrieval information corresponding to the first encoding information is a correct answer.

Moreover, if the communication unit receives the first retrieval information corresponding to the first encoding information from the user terminal 10, the brain signal measurement unit 110 may measure the user's brain signal, the preprocessing unit 120 may preprocess the user's brain signal (Preprocessed EEG), and the preprocessing unit 120 may extract theta waves from the user's preprocessed brain signal through power spectrum analysis (Feature Estimation).

The memory ability determination unit 130 may determine the user's short-term memory ability based on the extracted theta waves.

That is, the memory ability determination unit 130 may determine the user's short-term memory ability based on the first retrieval information corresponding to the first encoding information received by the communication unit from the user terminal 10.

The memory ability determination unit 130 may perform prediction models.

Here, the prediction models can be composed of a support vector machine (SVM), a multilayer perceptron (MLP), and a convolutional neural network (CNN). In particular, the structure of the convolutional neural network (CNN) can be seen from FIG. 4.

More specifically, the support vector machine (SVM) may use a radial basis function kernel SVM and may be configured with 6 frequency domains for 60 channels.

The multilayer perceptron (MLP) may be composed of three fully connected layers (360-180-90) and can use a rectified linear unit (ReLU) as the activation function and dropout (p=0.3), the Softmax function to classify into two classes of remembered and forgotten items, and a batch size of 20 for 50 epochs and cross entropy loss with 10 5 learning rate.

The convolutional neural network (CNN) can map electroencephalogram channels in a 2D form to maximize the spatial information of brain activity.

The memory ability determination unit 130 may predict the user's long-term memory ability based on the user's short-term memory ability previously determined through the above-described prediction models.

The communication unit may receive third retrieval information corresponding to the first encoding information from the user terminal 10 within a predetermined reference time. Here, the predetermined reference time may be defined as 24 hours as can be seen from FIG. 3, but this is for the convenience of illustration, and is not limited to 24 hours.

Moreover, the brain signal measurement unit 110 may measure the user's brain signal (hereinafter referred to as a fourth brain signal) if the communication unit receives the third retrieval information corresponding to the first encoding information from the user terminal 10 within a predetermined reference time.

Furthermore, the memory ability determination unit 130 may determine the user's long-term memory ability based on the extraction result of theta waves (hereinafter referred to as a fourth theta wave extraction result) extracted by the preprocessing unit 120 from the measurement result of the fourth brain signal.

Here, the memory ability determination unit 130 may compare the long-term memory ability predicted through the prediction models (hereinafter referred to as the predicted long-term memory ability) and the long-term memory ability determined through the fourth theta wave extraction result (hereinafter referred to as the determined long-term memory ability) to determine whether they match using Equation 2 below:

$$K = \frac{p_0 - p_e}{1 - p_e} \qquad \text{Equation 2}$$

In Equation 2, $p_0$ may represent the accuracy of prediction, and $p_e$ may represent the probability of the actual label matching the predicted label.

Here, the actual label pertains to the determined long-term memory ability, and the predicted label pertains to the predicted long-term memory ability.

Moreover, the memory ability determination unit 130 may analyze the difference between the predicted long-term memory ability and the determined long-term memory ability through Equation 2 above and reflect the analysis results to the prediction models, thereby improving the prediction accuracy of the prediction models.

The brain signal measurement unit 110 may measure the user's brain signal (hereinafter referred to as the fourth brain signal) if the communication unit receives the third retrieval information corresponding to the first encoding information from the user terminal 10 within a predetermined reference time.

Furthermore, the memory ability determination unit 130 may determine the user's long-term memory ability based on the extraction result of theta waves (hereinafter referred to as the fourth theta wave extraction result) extracted by the preprocessing unit 120 from the measurement result of the fourth brain signal.

The learning method providing unit 140 may provide a learning method tailored to the user's long-term memory ability.

Moreover, the learning method providing unit 140 may also provide a learning method tailored to the user's short-term memory ability, indicating that the learning method providing unit 140 can provide the user with a learning method optimized for the user's short-term memory ability and long-term memory ability.

The storage unit 150 may store information about the user's memory ability determined by the memory ability determination unit 130.

The memory ability determination unit 130 may classify the determination results of the user's memory ability based on a predetermined classification criterion, and the storage unit 150 may store the classification result of the memory ability determination unit 130.

Using the classification result, the memory ability determination unit 130 can improve the prediction accuracy of the above-described prediction models.

Additionally, the memory ability determination unit 130 may compare the first theta wave extraction result and the second theta wave extraction result and determine the user's memory ability based on the comparison result.

More specifically, the brain signal measurement unit 110 may measure the user's brain signal (i.e., the first brain signal) for the initial retrieval (i.e., the first retrieval) corresponding to the initial encoding, and the preprocessing unit 120 may extract theta waves from the measurement result of the first brain signal.

The brain signal measurement unit 110 may measure the user's brain signal (i.e., the second brain signal) for the encoding information provided to the user for the second time, and the preprocessing unit 120 may extract theta waves from the measurement result of the second brain signal.

The memory ability determination unit 130 may compare the extraction result of theta waves (i.e., the first theta wave extraction result) from the measurement result of the first brain signal from the preprocessing unit 120 and the extraction result of theta waves (i.e., the second theta wave extraction result) from the measurement result of the second brain signal from the preprocessing unit 120.

This allows the memory ability determination unit 130 to determine the user's memory ability.

To be more specific, based on the first theta wave extraction result, the memory ability determination unit 130 can determine the user's brain signal and the user's memory ability at the time of receiving the initial retrieval information.

Moreover, based on the second theta wave extraction result, the memory ability determination unit 130 can determine the user's brain signal and the user's memory ability at the time of receiving the second encoding information.

This allows the memory ability determination unit 130 to determine the user's memory ability in more detail and accurately determine the user's memory ability based on at least one of the brain activation result, the performance, and the response time at each point in time.

The learning method providing unit 140 may provide a learning method tailored to the user based on the comparison result of the memory ability determination unit 130, thereby providing a learning method optimized for the user's memory ability.

Moreover, the memory ability determination unit 130 may determine the user's memory ability if the second retrieval information corresponding to the second encoding information is a correct answer.

If the memory ability determination unit 130 determines that the second retrieval information corresponding to the second encoding information received from the user terminal 10 is not a correct answer, the communication unit may receive fourth retrieval information corresponding to the second encoding information from the user terminal 10.

Here, the fourth retrieval information corresponds to the second encoding information and may refer to a case where it is a correct answer.

The brain signal measurement unit 110 may measure the user's brain signal (hereinafter referred to as a fifth brain signal) if the communication unit receives the fourth retrieval information corresponding to the second encoding information from the user terminal 10.

The memory ability determination unit 130 may determine the user's memory ability based on the extraction result of theta waves (hereinafter referred to as a fifth theta wave extraction result) extracted by the preprocessing unit 120 from the measurement result of the fifth brain signal.

That is, if it is determined that the second retrieval information corresponding to the second encoding information received from the user terminal 10 is not a correct answer, it may receive new retrieval information to more accurately determine the user's memory ability.

Referring to FIGS. 5A, 5B and 5C, it is possible to find the details about encoding and retrieval, along with the details about the brain activation result, the performance, and the response time.

More specifically, throughout the entire specification, the term "encoding information" refers to the encoding process, signifying the initial experience of recognizing and learning new information in the brain.

Moreover, throughout the entire specification, the term "retrieval information" refers to the retrieval process, signifying the mental process of retrieving previously learned information.

In other words, these encoding and retrieval processes play a critical role in learning and decision-making, signifying a comprehensive cognitive process in which the brain recognizes and learns new information and retrieves previously learned information.

In more detail, referring to FIG. 5A, it can be seen that the user terminal 10 can output the first encoding information that can be received from the communication unit through a display and can input the first retrieval information corresponding to the first encoding information through an input device such as a touch screen.

Here, it can be seen from FIG. 5A that the first encoding information may refer to vocabulary encoding and the first retrieval information may refer to vocabulary retrieval.

Referring to FIG. 5B, it can be seen that the user terminal 10 can output the second encoding information that can be received from the communication unit through the display and can input the second retrieval information corresponding to the second encoding information through an input device such as a touch screen.

Here, it can be seen from FIG. 5B that the second encoding information may refer to vocabulary re-encoding and the second retrieval information may refer to vocabulary re-retrieval.

If the second retrieval information corresponding to the second encoding information input by the user terminal 10 is not a correct answer, the user terminal 10 may output the incorrect vocabulary/the number of repetitions through the display.

The user terminal 10 may transmit the incorrect vocabulary/the number of repetitions output through the display to the communication unit.

Here, for the convenience of illustration, the terms "vocabulary" and "incorrect vocabulary" are used herein; however, there terms are not limited to vocabulary in the encoding and retrieval processes for learning, and the above-described invention can be implemented similarly for other learning topics.

The term "incorrect vocabulary" may refer to the second retrieval information if the second retrieval information corresponding to the second encoding information is not a correct answer, and the number of repetitions may represent the number of times the second retrieval information, which does not correspond to the second encoding information and is not the correct answer, is input.

The memory ability determination unit 130 may determine the user's memory ability based on the incorrect vocabulary/the number of repetitions received by the communication unit from the user terminal 10.

Referring to FIG. 5C, the user terminal 10 can output the brain activation result, the performance, and the response time through the display.

That is, if the communication unit receives at least one of the first retrieval information and the second retrieval information from the user terminal 10, the brain signal measurement unit 110 can measure the user's brain signal, the preprocessing unit 120 can extract theta waves through power spectrum analysis from the user's brain signal measured by the brain signal measurement unit 110, and the memory ability determination unit 130 can determine the user's memory ability based on the theta waves extracted by the preprocessing unit 120.

Here, if the communication unit receives at least one of the first retrieval information and the second retrieval information from the user terminal 10, the memory ability determination unit 130 can determine at least one of the user's brain activation result, the performance, and the response time at that point in time, and then determine the user's memory ability based on this.

Moreover, the communication unit may transmit the determination result of at least one of the user's brain activation result, the performance, and the response time at that point in time determined by the memory ability determination unit 130 to the user terminal 10, and the user terminal 10 may output the determination result of at least one of the user's brain activation result, the performance, and the response time at that point in time determined by the memory ability determination unit 130, which has been received from the communication unit, through the display Here, as can be seen from FIG. 5C, the brain activation result can be represented by the size of theta waves (Theta power [dB]), and the performance can be represented by the accuracy percentage (%) of the first retrieval information for the first encoding information and the second retrieval information for the second encoding.

In this context, for precision comparison, the first encoding information and the second encoding information may mean the same thing, and similarly, the first retrieval information and the second retrieval information may mean the same thing.

The response time may refer to the time it takes to input first retrieval information for the first encoding information from the user terminal 10 or the time it takes to input the second retrieval information for the second encoding from the user terminal 10.

Figure 6:
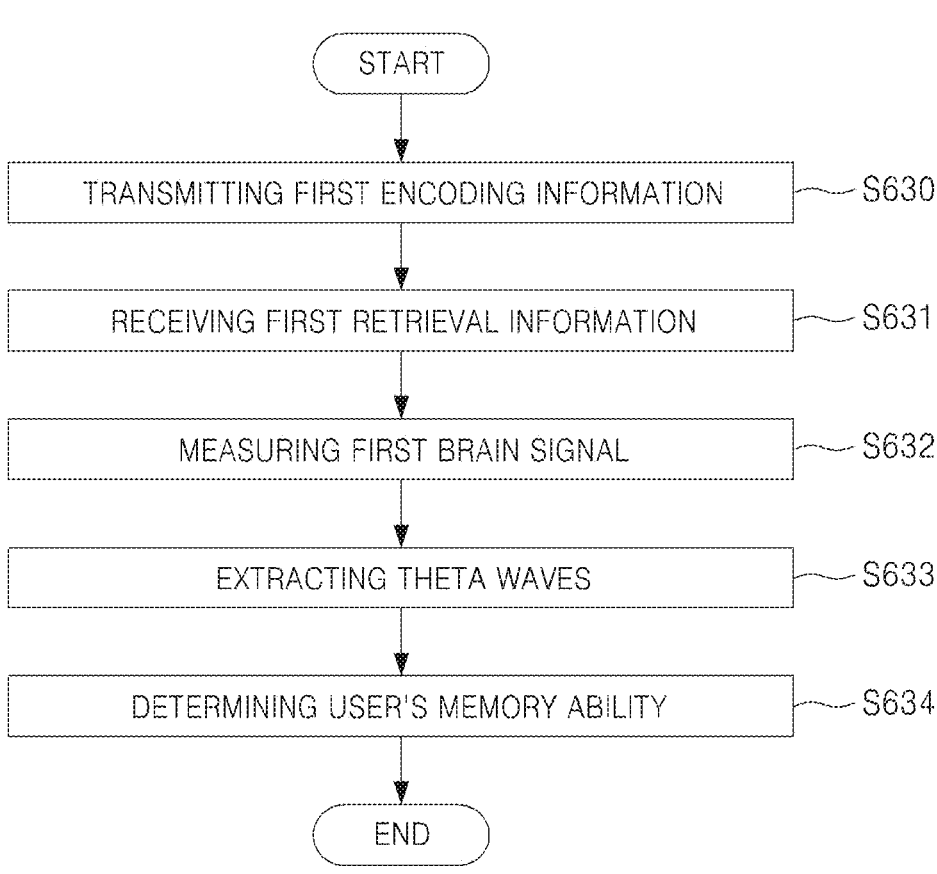
FIG. 6 is a flowchart illustrating the main steps of a method for memory enhancement based on electroencephalogram according to a second embodiment of the present invention.

FIG. 6 is a flowchart illustrating the main steps of a method for memory enhancement based on electroencephalogram according to a second embodiment of the present invention.

Referring to FIG. 6, the method for memory enhancement based on electroencephalogram may include the step of transmitting, by a communication unit, first encoding information to the user terminal 10 (S630).

Then, the communication unit may receive first retrieval information corresponding to the first encoding information from the user terminal 10 (S631).

If the communication unit receives the first retrieval information corresponding to the first encoding information from the user terminal 10, the brain signal measurement unit 110 may measure the user's brain signal (hereinafter referred to as a first brain signal) (S632).

Subsequently, the preprocessing unit 120 may extract theta waves from the first brain signal (S633).

Then, the memory ability determination unit 130 may determine the user's memory ability based on the extraction result of theta waves (hereinafter referred to a first theta wave extraction result) extracted by the preprocessing unit 120 from the measurement result of the first brain signal (S634).

Although the embodiments of the present invention have been described with reference to the accompanying drawings, those skilled in the art to which the present invention pertains can understand that the present disclosure can be implemented in other specific forms without changing the technical spirit or essential features thereof. Therefore, the embodiments described above should be understood as illustrative in all respects and not restrictive.

BRIEF DESCRIPTION OF REFERENCE NUMERALS

10: user terminal
100: apparatus for memory enhancement based on electroencephalogram
110: brain signal measurement unit
120: preprocessing unit
130: memory ability determination unit
140: learning method providing unit
150: storage unit

What is claimed is:

1. An apparatus for memory enhancement based on electroencephalogram, the apparatus comprising:

a brain signal measurement unit that measures a user's brain signal;

a preprocessing unit that extracts theta waves from the brain signal through power spectrum analysis;

a memory ability determination unit that determines a user's memory ability based on the theta waves extracted by the preprocessing unit;

a communication unit that transmits first encoding information to a user terminal and receives first retrieval information corresponding to the first encoding information from the user terminal; and a learning method providing unit that provides a learning method tailored to the user's memory ability based on a determination result by the memory ability determination units, wherein the brain signal measurement unit measures a first brain signal if the communication unit receives the first retrieval information corresponding to the first encoding information from the user terminal, wherein the memory ability determination unit determines a memory ability based on a first theta waves extraction result extracted by the preprocessing unit from a measurement result of the first brain signal, wherein the communication unit receives third retrieval information corresponding to the first encoding information from the user terminal within a predetermined reference time if a memory ability determined by the memory ability determination unit is a short-term memory ability, wherein the brain signal measurement unit measures a fourth brain signal if the communication unit receives the third retrieval information corresponding to the first encoding information from the user terminal within the predetermined reference time, wherein the memory ability determination unit determines a memory ability as a long-term memory ability based on a fourth theta wave extraction result extracted by the preprocessing unit from a measurement result of the fourth brain signal, wherein the learning method providing unit provides a learning method tailored to the long-term memory ability, and wherein encoding information includes information for memorization, and retrieval information includes an answer to the information for memorization.

2. The apparatus for memory enhancement based on electroencephalogram of claim 1, wherein the memory ability determination unit determines a memory ability based on at least one of a brain activation result measured by the brain signal measurement unit, a performance according to the brain activation result, and a response time according to the brain activation result.

3. The apparatus for memory enhancement based on electroencephalogram of claim 1, wherein the communication unit transmits second encoding information to the user terminal and receives second retrieval information corresponding to the second encoding information from the user terminal, wherein the brain signal measurement unit measures a second brain signal if the communication unit transmits the second encoding information to the user terminal and measures a third brain signal if the communication unit receives the second retrieval information corresponding to the second encoding information from the user terminal, and wherein the memory ability determination unit determines a memory ability based on a second theta waves extraction result extracted by the preprocessing unit from a measurement result of the second brain signal and determines a memory ability based on a third theta waves extraction result extracted by the preprocessing unit from a measurement result of the third brain signal.

4. The apparatus for memory enhancement based on electroencephalogram of claim 1, wherein the brain signal measurement unit is configured in the form of a headband that the user can wear, and wherein an electroencephalogram sensor is attached to the inner side of the headband to measure the user's brain signal, and Velcro is attached to the outer side of the headband.

5. The apparatus for memory enhancement based on electroencephalogram of claim 1, the apparatus further comprising a storage unit that stores information about the user's memory ability determined by the memory ability determination unit, wherein the memory ability determination unit classifies determination results of the user's memory ability based on a predetermined classification criterion, and wherein the storage unit stores a classification result by the memory ability determination unit.

6. The apparatus for memory enhancement based on electroencephalogram of claim 3, wherein the memory ability determination unit compares the first theta wave extraction result and the second theta wave extraction result and determines a memory ability based on a comparison result.

7. The apparatus for memory enhancement based on electroencephalogram of claim 3, wherein the communication unit receives fourth retrieval information corresponding to the second encoding information from the user terminal if the memory ability determination unit determines that the second retrieval information corresponding to the second encoding information received from the user terminal is not a correct answer, wherein the brain signal measurement unit measures a fifth brain signal if the communication unit receives the fourth retrieval information corresponding to the second encoding information from the user terminal, and wherein the memory ability determination unit determines a memory ability based on a fifth theta waves extraction result extracted by the preprocessing unit from a measurement result of the fifth brain signal.

8. The apparatus for memory enhancement based on electroencephalogram of claim 6, wherein the learning method providing unit provides a learning method tailored to the user based on the comparison result of the memory ability determination unit.

9. A method for memory enhancement based on electroencephalogram, the method comprising the steps of:

transmitting, by a communication unit, first encoding information to a user terminal;

receiving, by the communication unit, first retrieval information corresponding to the first encoding information from the user terminal;

measuring, by a brain signal measurement unit, a first brain signal if the communication unit receives the first retrieval information corresponding to the first encoding information from the user terminal;

extracting, by a preprocessing unit, a first theta waves from the first brain signal;

determining, by a memory ability determination unit, a memory ability based on a first theta waves extraction result extracted by the preprocessing unit from a measurement result of the first brain signal;

receiving, by the communication unit, third retrieval information corresponding to the first encoding information from the user terminal within a predetermined reference time if a memory ability determined by the memory ability determination unit is a short-term memory ability;

measuring, by the brain signal measurement unit, a fourth brain signal if the communication unit receives the third retrieval information corresponding to the first encoding information from the user terminal within the predetermined reference time;

determining, by the memory ability determination unit, a memory ability as a long-term memory ability based on a fourth theta wave extraction result extracted by the preprocessing unit from a measurement result of the fourth brain signal; and providing, by the learning method providing unit, a learning method tailored to the long-term memory ability, wherein encoding information includes information for memorization, and retrieval information includes an answer to the information for memorization.

* * * * *